US008932538B2

(12) United States Patent
Kim et al.

(10) Patent No.: US 8,932,538 B2
(45) Date of Patent: Jan. 13, 2015

(54) APPARATUS FOR ANALYZING SAMPLE

(75) Inventors: Hyun Min Kim, Gwangju-si (KR); Do Gyoon Kim, Seongnam-si (KR); Jong Myeon Park, Incheon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 459 days.

(21) Appl. No.: 13/007,192

(22) Filed: Jan. 14, 2011

(65) Prior Publication Data

US 2011/0176963 A1 Jul. 21, 2011

(30) Foreign Application Priority Data

Jan. 15, 2010 (KR) ........................ 10-2010-0004092

(51) Int. Cl.
*G01N 33/00* (2006.01)
*B01L 3/00* (2006.01)

(52) U.S. Cl.
CPC ..... *B01L 3/502746* (2013.01); *B01L 3/502738* (2013.01); *B01L 2200/0642* (2013.01); *B01L 2200/141* (2013.01); *B01L 2300/021* (2013.01); *B01L 2300/022* (2013.01); *B01L 2300/0803* (2013.01); *B01L 2400/0409* (2013.01); *B01L 2400/086* (2013.01)
USPC ............ 422/415; 422/408; 422/414; 422/502

(58) Field of Classification Search
USPC .................................. 422/408, 415, 414, 502
See application file for complete search history.

(56) References Cited

U.S. PATENT DOCUMENTS

| | | | | |
|---|---|---|---|---|
| 4,225,558 | A * | 9/1980 | Peterson et al. | 422/72 |
| 2002/0137218 | A1 | 9/2002 | Mian et al. | |
| 2006/0185584 | A1 | 8/2006 | Kim et al. | |
| 2007/0009391 | A1 | 1/2007 | Bedingham et al. | |
| 2007/0280857 | A1 | 12/2007 | Song et al. | |
| 2009/0053108 | A1 | 2/2009 | Cho et al. | |

OTHER PUBLICATIONS

International Search Report (PCT/ISA/210) dated Sep. 27, 2011, in International Application No. PCT/KR2010/009285.

* cited by examiner

*Primary Examiner* — Sam P Siefke
(74) *Attorney, Agent, or Firm* — Sughrue Mion, PLLC

(57) ABSTRACT

A apparatus for analyzing sample to prevent a sample from being stuck to a surface of the apparatus for analyzing sample in the course of being injected into the apparatus for analyzing sample. The apparatus for analyzing sample includes a platform having a disk shape. The platform includes chambers and channels, a sample inlet hole which is formed in an outer surface the platform and through which a sample is injected into the platform; an opening which is formed in the outer surface of the platform and through which a residual of the sample, present on the outer surface of the platform around the sample inlet hole, is introduced into a receiving space isolated from the chambers and channels; and a barrier which is formed on the outer surface of the platform around a portion of the opening to prevent the residual of the sample from moving past the opening in a radial outward direction of the platform.

20 Claims, 6 Drawing Sheets

APPARATUS FOR ANALYZING SAMPLE

CROSS-REFERENCE TO RELATED APPLICATION

This application claims priority from Korean Patent Application No. 10-2010-0004092, filed on Jan. 15, 2010 in the Korean Intellectual Property Office, the disclosure of which is incorporated herein by reference.

BACKGROUND

1. Field

Apparatuses consistent with exemplary embodiments relate to a apparatus for analyzing sample to perform a biochemical process on a sample.

2. Description of the Related Art

Generally, a device used to implement a biological or chemical reaction using a small quantity of fluid is referred to as apparatus for analyzing sample. Such a apparatus for analyzing sample includes microfluidic structures arranged in a platform that may have various shapes, e.g., chip and disk shapes.

Microfluidic structures include a chamber which contains a fluid, a channel for fluid flow, and a valve to control the fluid flow. The chamber, channel and valve may be arranged according to various configurations within the platform.

A so-called biochip is designed to implement tests including biochemical reactions on a small-sized chip, in which microfluidic structures are arranged in a chip-shaped platform. In particular, a device to implement several operations on a single chip is referred to as a lab-on-a chip.

Transferring a fluid in microfluidic structures requires a drive pressure, such as a capillary pressure or a pressure produced by a separate pump. Recently, apparatus for analyzing sample in which microfluidic structures are arranged in a disk-shaped platform and a fluid is moved through the microfluidic structures by centrifugal force to enable implementation of a series of operations, have been proposed. Such a microfluidic device is referred to as a lab compact disc (CD) or lab-on a CD.

A sample injected into the apparatus for analyzing sample based on centrifugal force is moved in a direction away from a rotation center of the microfluidic device by centrifugal force.

The sample is injected through an inlet hole of the apparatus for analyzing sample via an injection tool, e.g., a pipet or syringe. However, injecting the sample using a pipet or syringe may cause the sample to be stuck around the inlet hole.

The sample, especially a biological sample, stuck around the inlet hole may contaminate a surface of the apparatus for analyzing sample. In addition, if the microfluidic device containing the sample is mounted in a sample testing apparatus, a small quantity of the sample may contaminate interior elements of the sample testing apparatus, such as a light source, etc., during rotation of the microfluidic device. If the sample is stuck to the light source or an outer surface of a testing chamber, this may cause an error in results of the microfluidic device.

In addition, if a sample containing disease-causing agents is injected into the apparatus for analyzing sample, a residual sample on the surface of the microfluidic device may cause secondary infection.

SUMMARY

One or more exemplary embodiments provide a microfluidic device which is driven based on centrifugal force and prevents a sample from being stuck to a surface of the apparatus for analyzing sample in the course of being injected into the apparatus for analyzing sample.

One or more exemplary embodiments also provide a apparatus for analyzing sample based on centrifugal force to prevent, e.g., interior elements of a sample testing apparatus from being contaminated by a sample stuck to the apparatus for analyzing sample during rotation of the apparatus for analyzing sample.

In accordance with an aspect of an exemplary embodiment, there is provided a apparatus for analyzing sample including a platform having a disk shape, in which chambers and channels are defined, the platform including a sample inlet hole formed in an outer surface of the platform to inject the sample into the platform, an opening to introduce a residual sample into a receiving space isolated from the chambers and channels defined in the platform, and a barrier surrounding the opening to prevent the residual sample from moving in a radial outward direction of the platform.

The apparatus for analyzing sample may further include a sloped portion inclined downward in the radial outward direction between the sample inlet hole and the opening.

The apparatus for analyzing sample may further include a guide portion to guide the residual sample, present on an outer surface of the platform around the sample inlet hole, in the radial outward direction.

The apparatus for analyzing sample may further include a protruding portion surrounding the sample inlet hole to prevent overflow of the residual sample.

The platform may include a residual sample receptacle to receive the residual sample moved from the opening into the platform.

The residual sample receptacle may include a predetermined region stepped downward from an inner bottom surface of the platform.

The chambers may include a sample chamber in which the sample injected through the sample inlet hole is received, and an overflow chamber to receive an excess of the sample when the sample is excessively injected into the sample chamber.

An upper end of the barrier may be bent toward the opening.

In accordance with an aspect of another exemplary embodiment, there is provided a apparatus for analyzing sample including a platform having a disk shape, the platform including a sample inlet hole to inject the sample into the platform, a residual sample receptacle provided at a radially outward position of the sample inlet hole, and a barrier to prevent a residual sample to be introduced into the residual sample receptacle from moving outward from the residual sample receptacle.

The residual sample receptacle may include a receiving space defined in the platform.

The platform may include an opening to communicate an outer surface of the platform with the receiving space.

The platform may include a first substrate in which a chamber and channel are formed, and a second substrate coupled to the first substrate to define the chamber and channel, and the residual sample receptacle may be formed in at least one of the first and second substrates.

The apparatus for analyzing sample may further include a sloped portion to allow the residual sample around the sample inlet hole to be smoothly moved into the residual sample receptacle.

The apparatus for analyzing sample may further include a guide portion to guide the residual sample, present on an outer surface of the platform around the sample inlet hole, to the residual sample receptacle.

A width of the guide portion may gradually increase in a radial outward direction from the sample inlet hole.

The chamber may include a sample chamber communicating with the sample inlet hole, and the residual sample receptacle may be defined in the platform so as to be separated from the sample chamber.

An upper end of the barrier may be bent in a radial inward direction of the platform.

BRIEF DESCRIPTION OF THE DRAWINGS

The above and/or other aspects will become apparent and more readily appreciated from the following description of exemplary embodiments, taken in conjunction with the accompanying drawings of which.

DETAILED DESCRIPTION

Figure 1:
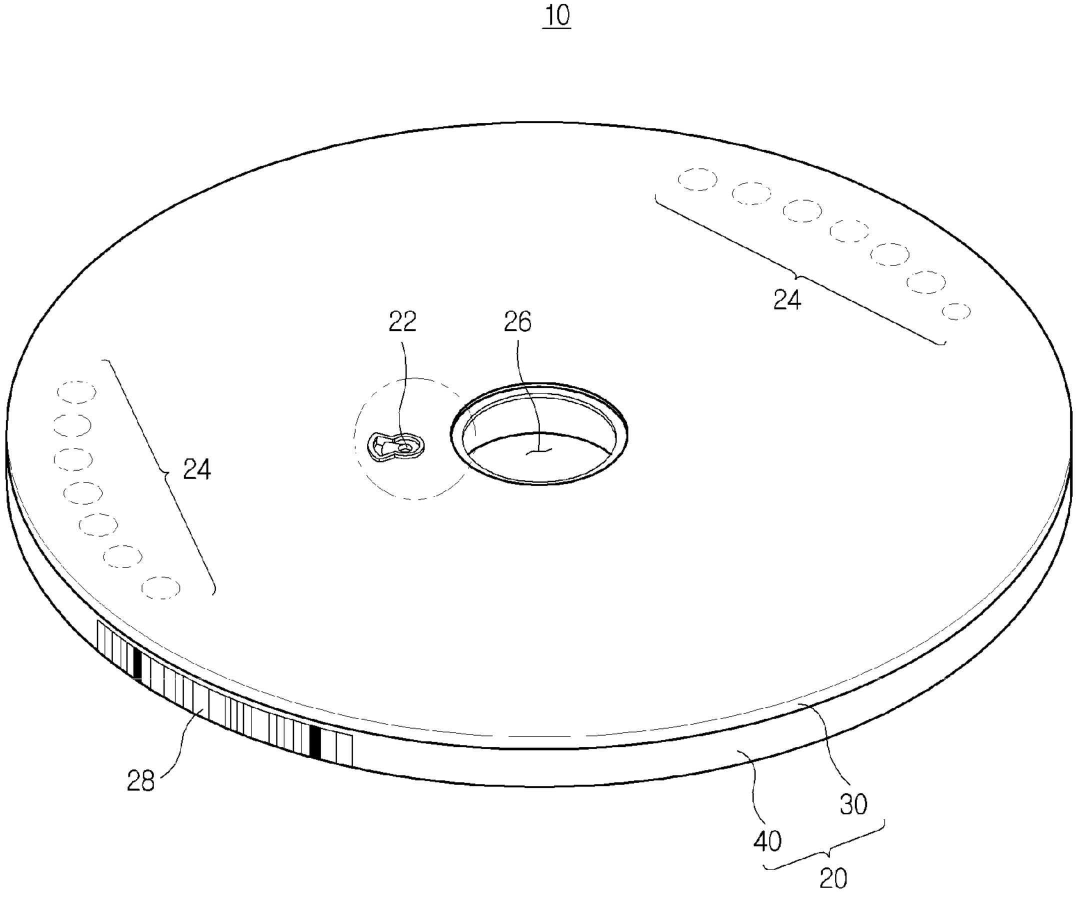
FIG. 1 is a perspective view illustrating a apparatus for analyzing sample according to an exemplary embodiment.

Reference will now be made in detail to a apparatus for analyzing sample and a sample testing apparatus using the same according to exemplary embodiments, examples of which are illustrated in the accompanying drawings, wherein like reference numerals refer to like elements throughout.

In the drawings, structures, such as chambers, channels, etc., may be illustrated in simplified shapes, and may be magnified or reduced differently from an actual size ratio thereof. In the terms, such as, e.g., “apparatus for analyzing sample” and “micro-particle”, “micro-” is used only in contrast to “macro-”, and should not be interpreted as being limited to any specific size.

FIG. 1 is a perspective view illustrating a apparatus for analyzing sample according to an exemplary embodiment.

Referring to FIG. 1, the apparatus for analyzing sample 10 includes a rotatable disk-shaped platform 20.

The platform 20 may be made of plastics which are easy to mold and have biologically inert superficial properties, such as acryl, polydimethylsiloxane (PDMS), etc., but embodiments are not limited thereto, and other materials having chemical and biological stability and excellent optical transparency and mechanical processability may be utilized.

The platform 20 may include multiple layers of plates. By providing interfaces of the contact plates with intagliated structures corresponding to, e.g., chambers and channels and bonding the plates to each other, the chambers and channels may be defined in the platform 20.

For example, the platform 20 may include a first substrate 30 and a second substrate 40 attached to the first substrate 30, or may further include a partition interposed between the first substrate 30 and the second substrate 40 to define chambers to receive a fluid therein and channels for fluid flow. Of course, the platform 20 may have various other configurations. The first substrate 30 and second substrate 40 may be made of thermoplastic resin.

Bonding of the first substrate 30 and second substrate 40 may be accomplished by various methods, such as adhesion using an adhesive or a double-sided tape, ultrasonic fusion, laser welding, etc.

The apparatus for analyzing sample 10 may include microfluidic structures, i.e. chambers, channels providing fluid flow passages and valves to open or close the channels, formed in the platform 20. For example, arrangement of the chambers, channels and valves is determined in conformity to biochemical processes, such as, e.g., centrifugal separation of a fluidic sample, immune serum reaction, gene analysis, gene extraction and gene amplification.

In one example, the apparatus for analyzing sample 10 includes structures for performing biochemical processes of a sample including, e.g., culturing, mixing, separation and enrichment of a sample. The structures for the biochemical processes may include, e.g., a sample inlet hole 22 through which a fluid required for the biochemical processes, such as, e.g., a biochemical sample is injected from an external source into the apparatus for analyzing sample 10, channels (not shown) for fluid flow, chambers (not shown) which contains a fluid therein, reaction regions 24 in which biochemical reactions of a sample occur, and valves (not shown) to control fluid flow. In the exemplary embodiment, the interior of the apparatus for analyzing sample 10 may be designed to have various configurations according to the use purpose thereof, and a description related to detailed arrangement relationship of the above described structures will be omitted herein.

Figure 2:
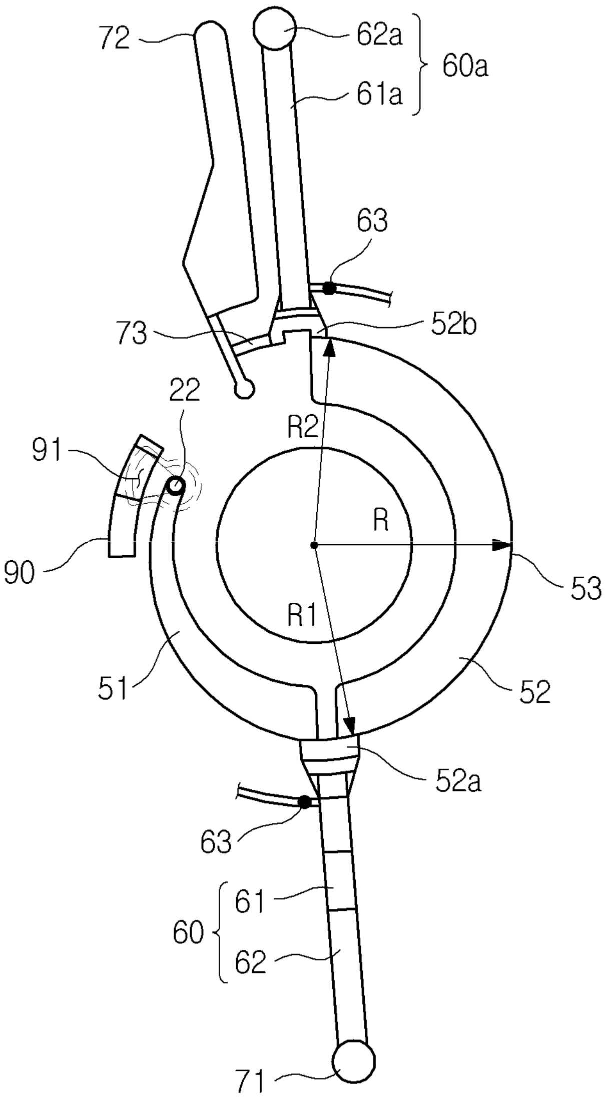
FIG. 2 is a detailed view illustrating a sample chamber and sample distributor included in the apparatus for analyzing sample according to an exemplary embodiment.

FIG. 2 is a detailed view illustrating a sample chamber and sample distributor included in the apparatus for analyzing sample according to an exemplary embodiment.

Now, the microfluidic structures arranged in the platform 20 will be described in brief with reference to FIGS. 1 and 2.

If it is assumed that an area radially close to a rotation center of the platform 20 is called “an inner area” and an area radially away from the rotation center is called “an outer area”, a sample chamber 51 is defined in an innermost area of the platform 20. The sample chamber 51 receives a sample therein and is provided with the sample inlet hole 22 through which the sample is injected into the apparatus for analyzing sample 10.

The sample may be supplied from the sample chamber 51 into first and second sample distributors 60 and 60*a*. The sample distributors 60 and 60*a* may have a predetermined capacity to gauge a constant quantity of sample required for a test. The sample distributors 60 and 60*a* are located more radial outward than the sample chamber 51 because centrifugal force generated by rotation of the platform 20 is used to move the sample from the sample chamber 51 to the sample distributors 60 and 60*a*. The sample distributors 60 and 60*a* may serve as a centrifugal separator that divide a sample (e.g., blood) into supernatant liquid and sediment using rotation of the platform 20. The sample distributors 60 and 60*a* for centrifugal separation may have various shapes. For example, as illustrated in FIG. 2, the sample distributors 60 and 60*a* may respectively include supernatant liquid collection channels 61 and 61*a* extending in a radial outward direction thereof, and sediment collection channels 62 and 62*a* located at distal ends of the supernatant liquid collection channels 61 and 61*a* to provide spaces to collect sediment having a high specific gravity.

The sample is first moved from the sample chamber 51 to the first sample distributor 60 to fill the first sample distributor

60, and then, is moved through a sample transfer chamber 52 to the second sample distributor 60*a* to fill the second sample distributor 60*a*.

The sample transfer chamber 52 includes a first connector 52*a* connected to the first sample distributor 60, and a second connector 52*b* connected to the second sample distributor 60*a*. The first and second connectors 52*a* and 52*b* may be provided at an outer wall 53 of the sample transfer chamber 52. A radial distance R2 between the rotation center and the second connector 52*b* may be greater than a radial distance R1 between the rotation center and the first connector 52*a*.

A curvature radius R of the outer wall 53 between the first connector 52*a* and the second connector 52*b* may be equal to or greater than the radial distance R1, and may be gradually increased from the first connector 52*a* toward the second connector 52*b*. With this configuration, if the apparatus for analyzing sample 10 is rotated, the sample is moved into the first sample distributor 60 by centrifugal force to fill the first sample distributor 60 and thereafter, is moved into the sample transfer chamber 52. Subsequently, the sample is moved along the outer wall 53 of the sample transfer chamber 52 by centrifugal force, thereby being moved into the second sample distributor 60*a* through the second connector 52*b*.

An overflow chamber 72 is provided to receive an excess of the sample and also, to confirm whether or not a sufficient quantity of sample for a test is supplied into the sample distributors 60 and 60*a*. The overflow chamber 72 is connected to an upper end of the second sample distributor 60*a* via a channel 73. After the sample of the sample chamber 51 is moved to fill the sample distributors 60 and 60*a* in sequence by way of the sample transfer chamber 52, an excess or residual of the sample (hereafter "a residual sample") is moved into the overflow chamber 72 through the channel 73.

Sample distribution channels 63 are arranged at one side of the respective supernatant liquid collection channels 61 and 61*a* to distribute collected supernatant liquid (e.g., serum when the sample is blood) into structures for use in a following step. The sample distribution channels 63 are connected to the supernatant liquid collection channels 61 and 61*a* via valves 64.

The valves 64 may be selected from various types of microfluidic valves. For example, valves to be passively opened upon receiving a predetermined or more pressure, such as capillary valves, may be employed, or valves to be actively opened upon receiving power or energy from an external source in response to operating signals may be employed. In the exemplary embodiment, the valves 64 are so-called normally closed valves that close the channels 63 to prevent fluid flow prior to being opened by application of energy, e.g., by absorbing electromagnetic energy.

A dilution chamber (not shown) in which a dilution buffer is received may be provided at the outside of the sample chamber 51, and in turn, the reaction regions 24 may be arranged at the outside of the dilution chamber to communicate with the dilution chamber. The reaction regions 24 may receive liquid-phase or dry solid-phase reagents.

In this manner, the sample of the sample chamber 51 may be introduced into the reaction regions 24 via various paths after sequentially passing through the sample distributors 60 and 60*a*, sample distribution channels 63 and dilution chamber (not shown). The sample introduced into the reaction regions 24 reacts with the reagents.

The disk-shaped apparatus for analyzing sample 10 may be coupled to a spindle motor (105, see FIG. 6) and thus, may be rotated at a high speed. The apparatus for analyzing sample 10 is centrally perforated with a hole 26 for mounting to the spindle motor 105. Centrifugal force generated by rotation of the spindle motor 105 may act to move the fluid remained in the chambers or channels of the apparatus for analyzing sample 10 toward the outer periphery of the platform 20.

A barcode 28 may be provided at an outer peripheral surface of the platform 20. The barcode 28 may contain various information, such as, e.g., fabrication date and expiration date of the apparatus for analyzing sample 10 as occasion demands.

The barcode 28 may be selected from various types of barcodes. For example, the barcode 28 may be a one-dimensional barcode, or a two-dimensional barcode (e.g., a matrix barcode) to store a great quantity of information.

Alternatively, the barcode may be replaced by a hologram, radio frequency identification (RFID) tag, or memory chip, used to store information therein. In this case, a sample testing apparatus may include a data reading unit 130 having a reader suitable to read information of various types of barcodes as will be described hereinafter.

In the case where the barcode is replaced by a storage medium, such as, e.g., a memory chip, to enable reading and writing of information, it may be possible to store identification information and other information related to sample testing results, patient information, blood collecting/testing date and time and execution of a test.

Figure 3:
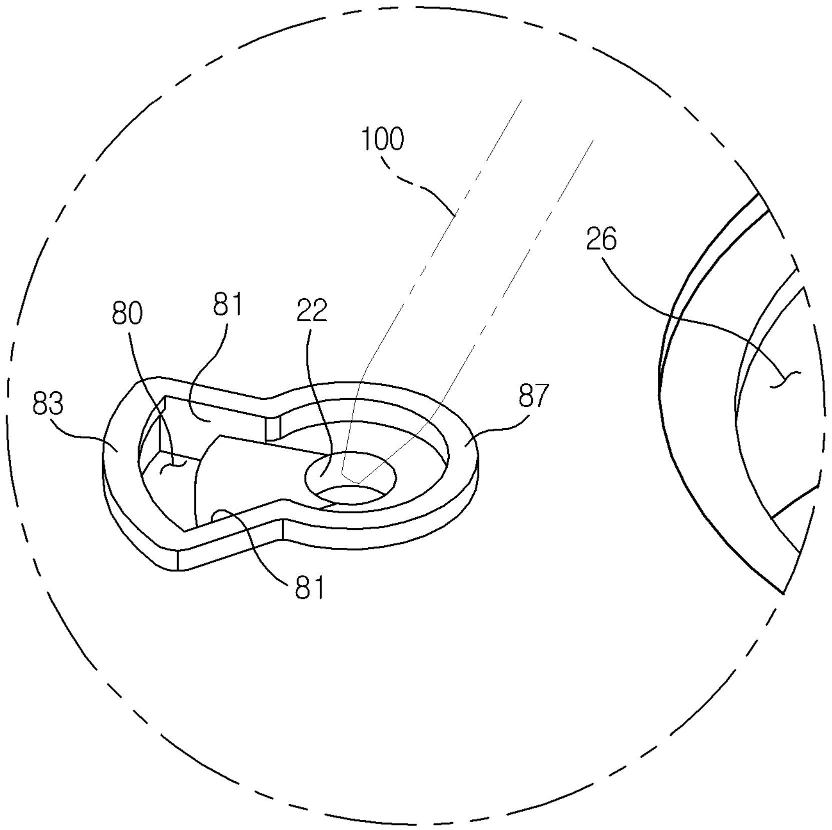
FIG. 3 is an enlarged view of a portion of FIG. 1.
Figure 4:
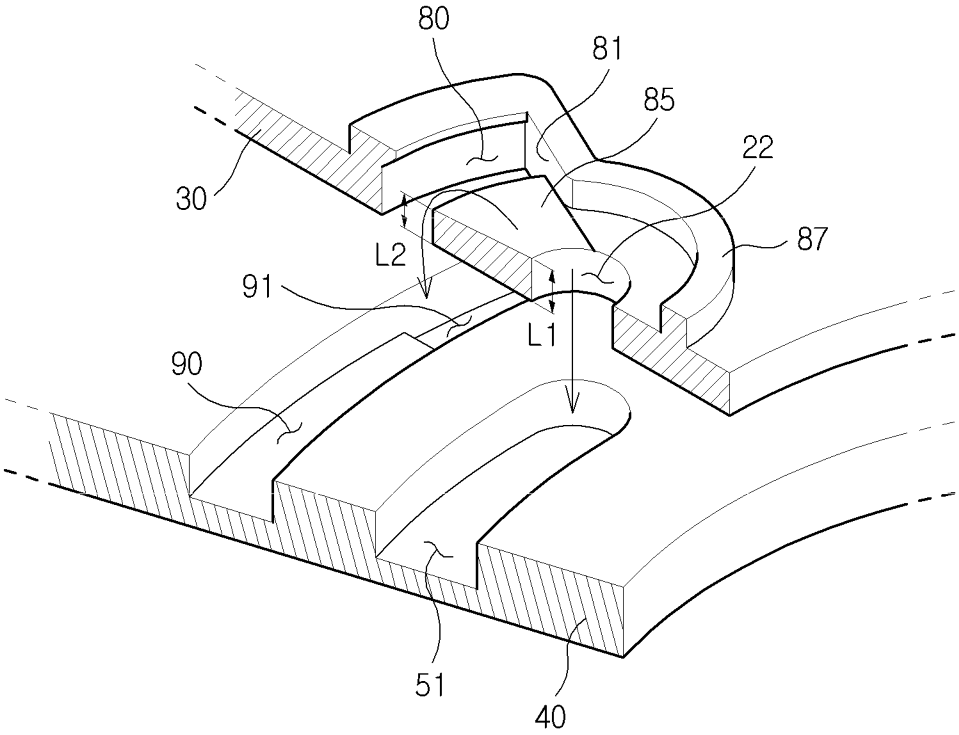
FIG. 4 is a partially cut-away perspective view of the sample chamber in a separated state of first and second substrates of the apparatus for analyzing sample according to an exemplary embodiment.
Figure 5:
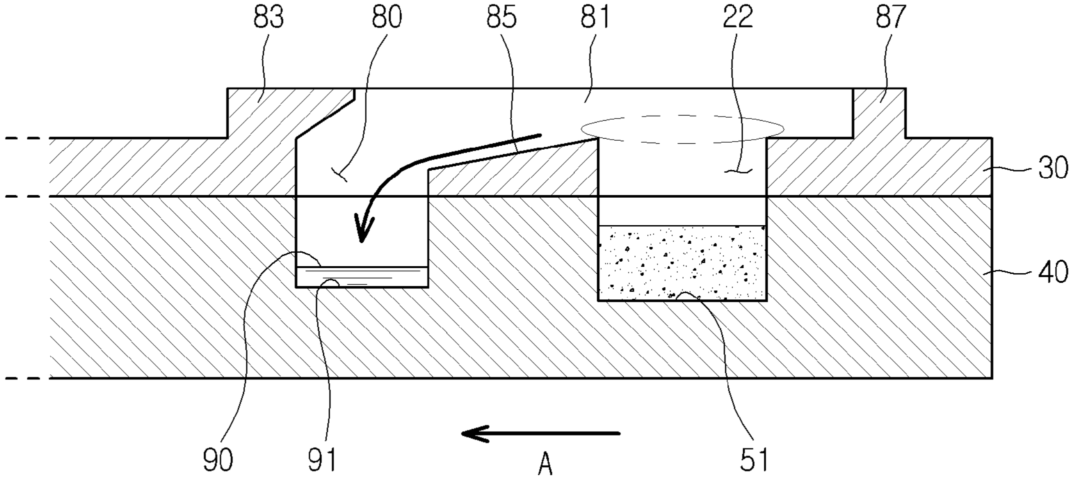
FIG. 5 is a view illustrating movement of a residual sample in the apparatus for analyzing sample according to the exemplary embodiment.

FIG. 3 is an enlarged view of a portion of the apparatus for analyzing sample of FIG. 1. FIG. 4 is a partially cut-away perspective view of the sample chamber in a separated state of first and second substrates of the apparatus for analyzing sample according to the exemplary embodiment. FIG. 5 is a view illustrating movement of a residual sample in the apparatus for analyzing sample according to the exemplary embodiment.

Referring to FIGS. 3 and 4, the apparatus for analyzing sample 10 may include a residual sample receptacle 90 to prevent a residual sample stuck around the sample inlet hole 22 from being scattered from an outer surface of the platform 20, a barrier 83 to prevent the residual sample from being moved in a radial outward direction of the platform 20, and a guide portion 81 to guide the residual sample around the sample inlet hole 22 into the residual sample receptacle 90.

In the exemplary embodiment, the residual sample receptacle 90 is isolated from the sample chamber 51 and other chambers and channels connected to the sample chamber 51, to prevent the residual sample from being mixed with the sample received in the chambers and channels. In addition, the residual sample receptacle 90 is located to prevent a person who performs a test from directly accessing the residual sample received in the residual sample receptacle 90 from the outside of the platform 20.

The first substrate 30 is provided with a protruding portion 87 surrounding the sample inlet hole 22 to prevent the residual sample from spreading outward from the sample inlet hole 22. The guide portion 81 extends fanwise about the sample inlet hole 22. Also, the guide portion 81 has a height corresponding to that of the protruding portion 87 to guide the residual sample into the residual sample receptacle 90 when the residual sample is moved in a radial outward direction by centrifugal force during rotation of the apparatus for analyzing sample 10.

The first substrate 30 is perforated with an opening 80 to introduce the residual sample into the residual sample receptacle 90 when the residual sample is moved in a radial outward direction during rotation of the apparatus for analyzing sample 10.

In this case, a sloped portion 85 is provided between the sample inlet hole 22 and the opening 80. The sloped portion 85 is inclined downward in a radial outward direction from the sample inlet hole 22 and thus, serves to facilitate movement of the residual sample from the sample inlet hole 22 to the opening 80.

The barrier 83 of the platform 20 is located at a radially outward position of the opening 80, to prevent the residual sample from moving in a radial outward direction beyond the opening 80 by rotation of the apparatus for analyzing sample 10, rather than entering the opening 80. An upper end of the barrier 83 is radially inwardly bent to enhance the above described effect of the barrier 83.

The residual sample receptacle 90 communicates with the opening 80 to receive the residual sample having passed through the opening 80. The residual sample receptacle 90 is formed in the second substrate 40, and may have a predetermined volume of receiving space 91 stepped downward from an bottom surface thereof.

Hereinafter, sequential operations of injecting the sample into the apparatus for analyzing sample 10 will be described. For example, to inject the fluidic sample, such as blood, into the apparatus for analyzing sample 10, a tool, such as a pipet 100, may be used. A distal end of the pipet 100 in which the sample is received is positioned close to the sample inlet 22.

The end of the pipet 100 is inserted into the sample inlet hole 22 to inject the sample received in the pipet 100 into the sample chamber 51. After completely injecting the sample into the sample chamber 51, the pipet 100 is separated from the sample inlet hole 22. Upon separation of the pipet 100, a residue of the sample may remain around the sample inlet hole 22.

If the apparatus for analyzing sample 10 with the residual sample remaining around the sample inlet hole 22 is injected into a sample testing apparatus and is rotated, as illustrated in FIG. 5, the residual sample stuck around the sample inlet hole 22 is moved to the opening 80 along the guide portion 81 by centrifugal force, and subsequently, is introduced into the residual sample receptacle 90 defined within the platform 20 through the opening 80.

In this manner, the residual sample present on an outer surface of the apparatus for analyzing sample 10 may be guided to a predetermined position, and this may prevent the residual sample from being scattered to unwanted positions.

Hereinafter, the sample testing apparatus to test the sample using the apparatus for analyzing sample according to the exemplary embodiment will be described.

Figure 6:
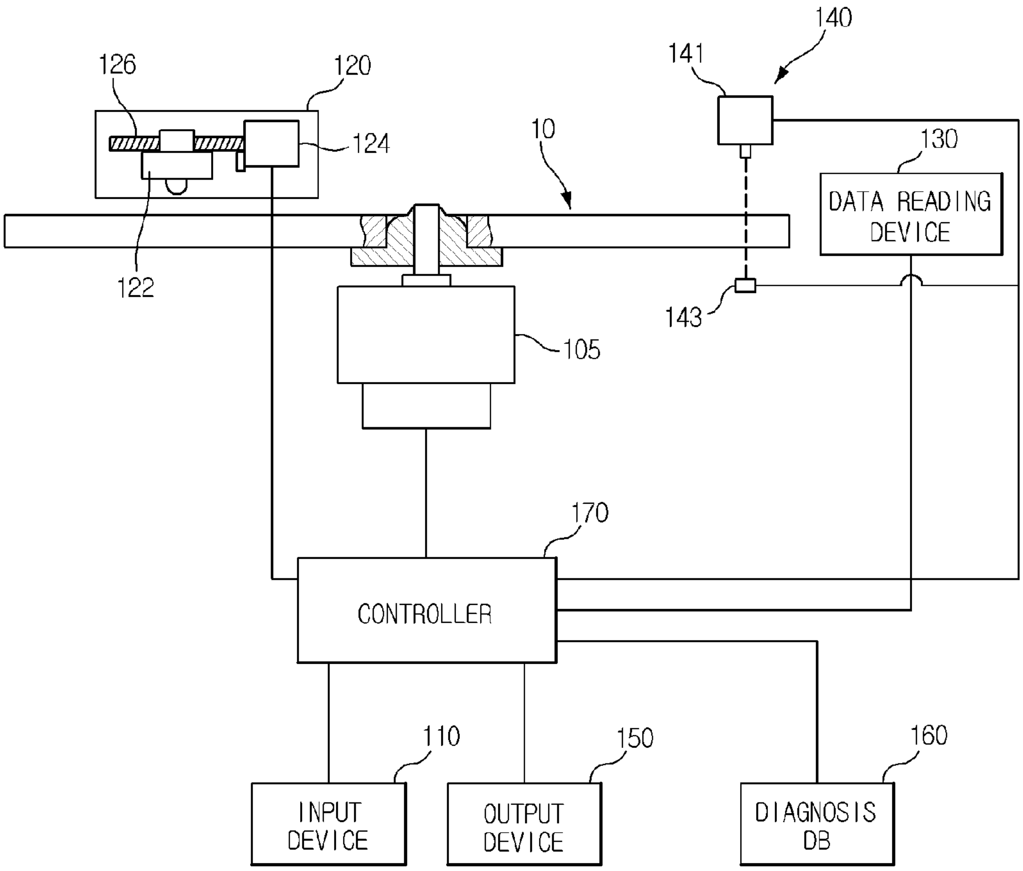
FIG. 6 is a block diagram illustrating a sample testing apparatus using the apparatus for analyzing sample according to the exemplary embodiment.

FIG. 6 is a block diagram illustrating the sample testing apparatus using the apparatus for analyzing sample according to the exemplary embodiment.

The sample testing apparatus according to the exemplary embodiment includes the spindle motor 105 to rotate the apparatus for analyzing sample 10, a data reading device 130, a valve opening device 120, an inspection device 140, an input device 110, an output device 150, a diagnosis database (DB) 160, and a controller 170 to control the above mentioned devices.

The spindle motor 105 may initiate or stop rotation of the apparatus for analyzing sample 10 to allow the apparatus for analyzing sample 10 to reach a specific position.

Although not shown, the spindle motor 105 may include a motor drive device to control an angular position of the apparatus for analyzing sample 10. For example, the motor drive device may utilize a step motor or DC motor.

The data reading device 130 may be, e.g., a barcode reader. The data reading device 130 reads data stored in the barcode 28 and transmits the data to the controller 170. The controller 170 operates the respective devices based on the read data, to drive the sample testing apparatus.

The valve opening device 120 opens or closes the valves 64 of the apparatus for analyzing sample 10. The valve opening device 120 may include an external energy source 122 and moving units 124 and 126 to move the external energy source 122 to a position corresponding to a valve that needs to be opened.

The external energy source 122 to radiate electromagnetic waves may be a laser light source to irradiate laser beam, or may be a light emitting diode or xenon lamp to irradiate visible or infrared light. In particular, the laser light source may include at least one laser diode.

The moving units 124 and 126 serve to regulate a position or orientation of the external energy source 122, so as to allow the external energy source 122 to focus energy to a desired region of the apparatus for analyzing sample, i.e. to the valve. The moving units 124 and 126 may respectively include a drive motor 124 and a gear 126 to move the external energy source 122 mounted thereon to a position above the valve to be opened, based on rotation of the drive motor 124. The moving units may be realized via various mechanisms.

The inspection device 140 may include at least one light emitting element 141 and a light receiving element 143 arranged to correspond to the light emitting element 141 and serving to receive light having passed through the reaction regions 24 of the apparatus for analyzing sample 10.

The light emitting element 141 is a light source to be turned on or off at a predetermined frequency. Examples of an available light source include semiconductor light emitting devices, such as a Light Emitting Diode (LED), Laser Diode (LD), etc., and gas discharge lamps, such as a halogen lamp, xenon lamp, etc.

The light emitting element 141 is positioned to allow light emitted from the light emitting element 141 to reach the light receiving element 143 by way of the reaction regions 24.

The light receiving element 143 is adapted to generate electric signals according to the intensity of incidence light. For example, the light receiving element 143 may be a depletion layer photo diode, Avalanche Photo Diode (APD), PhotoMultiplier Tubes (PMT), or the like.

The controller 170 controls the spindle motor 105, data reading device 130, valve opening device 120, inspection device 140, etc., to assure effective operations of the sample testing apparatus. Also, the controller 170 searches the diagnosis DB 160 for comparative analysis between information detected from the inspection device 140 and the diagnosis DB 160, thereby testing the presence of diseases of blood received in the reaction regions 24 of the apparatus for analyzing sample 10.

The input device 110 serves to input the kind of the sample introduced into the apparatus for analyzing sample 10 and/or possible testing items according to the kind of the injected sample, and may take the form of a touch screen provided at the sample testing apparatus.

The output device 150 serves to output the diagnosed results and the completion of operation. The output device 150 may be a visual output device, such as a Liquid Crystal Display (LCD), an audio output device, such as a speaker, or an audio-visual output device.

If the apparatus for analyzing sample 10 mounted in the sample testing apparatus is rotated in a state wherein the residual sample is stuck around the sample inlet hole 22, the residual sample stuck around the sample inlet hole 22 is moved to the opening 80 along the guide portion 81 by centrifugal force, and then, is introduced into the residual sample receptacle 90 defined in the platform 20 through the opening 80.

In this case, as the residual sample on the outer surface of the apparatus for analyzing sample 10 may be guided to a predetermined position, it may be possible to prevent the residual sample from being scattered to unspecified positions. Accordingly, for example, it may be possible to prevent the residual sample from remaining on the outer surface of the platform 20 on an optical path between the light emitting element 141 and the light receiving element 143, or to prevent the residual sample from being directly stuck to the light source of the external energy source 122, the light emitting element 141 and the light receiving element 143. This may prevent erroneous testing results.

The above described exemplary embodiment may also prevent contamination of interior elements of the sample testing apparatus due to the residual sample, or prevent an inspector from directly touching the residual sample.

As is apparent from the above description, a apparatus for analyzing sample using centrifugal force according to an exemplary embodiment adopts a residual sample receptacle to receive a residual sample remaining on an outer surface of the apparatus for analyzing sample, thereby preventing the residual sample from being exposed to the outside.

Further, since the residual sample stuck to the apparatus for analyzing sample may be collected into the residual sample receptacle during rotation of the apparatus for analyzing sample, it may be possible to prevent the residual sample from contaminating, e.g., interior elements of a sample testing apparatus.

Although a few exemplary embodiments have been shown and described, it would be appreciated by those skilled in the art that changes may be made in these exemplary embodiments without departing from the principles and spirit of the inventive concept, the scope of which is defined in the claims and their equivalents.

What is claimed is:

1. An apparatus for analyzing sample comprising:

a platform having a disk shape, the platform comprising:

a plurality of chambers;

a plurality of channels connecting the chambers;

a sample inlet hole which is formed in an outer surface of the platform and through which a sample is injected into the platform;

an opening which is formed in the outer surface of the platform and is arranged to receive a residual of the sample, present on the outer surface of the platform around the sample inlet hole, and to introduce the received residual of the sample into a receiving space isolated from the chambers and the channels; and a barrier which is formed on the outer surface of the platform around a portion of the opening to prevent the residual of the sample from moving past the opening in a radial outward direction of the platform.

2. The apparatus for analyzing sample according to claim 1, wherein the platform further comprises a sloped portion which is inclined downward in a radial outward direction between the sample inlet hole and the opening.

3. The apparatus for analyzing sample according to claim 1, wherein the platform further comprises a guide portion which guides the residual of the sample in the radial outward direction.

4. The apparatus for analyzing sample according to claim 1, wherein the platform further comprises a protruding portion surrounding a portion of the sample inlet hole to prevent overflow of the residual of the sample.

5. The apparatus for analyzing sample according to claim 1, wherein the platform further comprises a residual sample receptacle which includes the receiving space and receives the residual of the sample through the opening.

6. The apparatus for analyzing sample according to claim 5, wherein the residual sample receptacle includes a first region and a second region stepped downward from the first region, and the receiving space corresponds to the second region.

7. The apparatus for analyzing sample according to claim 1, wherein the chambers comprise a sample chamber which receives the sample injected through the sample inlet hole, and an overflow chamber which receives an excess of the sample when the sample is excessively injected into the sample chamber.

8. The apparatus for analyzing sample according to claim 1, wherein an upper end of the barrier is bent toward the opening.

9. An apparatus for analyzing sample comprising:

a platform having a disk shape, the platform comprising:

a chamber;

a sample inlet hole which is formed in an outer surface of the platform and through which a sample is injected to the chamber;

a residual sample receptacle which is provided at a position radially outward from the sample inlet hole and receives the residual of the sample present on the outer surface of the platform through an opening, the residual sample receptacle being isolated from the chamber; and a barrier which is formed on the outer surface of the platform to prevent the residual of the sample from moving outward from the residual sample receptacle.

10. The apparatus for analyzing sample according to claim 9, wherein the residual sample receptacle includes a receiving space defined in the platform.

11. The apparatus for analyzing sample according to claim 10, wherein the opening communicates with the receiving space.

12. The apparatus for analyzing sample according to claim 9, wherein:

the platform further comprises a first substrate and a second substrate coupled to the first substrate; and the residual sample receptacle is formed in at least one of the first and second substrates.

13. The apparatus for analyzing sample according to claim 11, wherein the platform further comprises a sloped portion which is inclined downward in a radial outward direction between the sample inlet hole and the opening.

14. The apparatus for analyzing sample according to claim 9, wherein the platform further comprises a guide portion which guides the residual of the sample, present on the outer surface of the platform around the sample inlet hole, in a radial outward direction to the residual sample receptacle.

15. The apparatus for analyzing sample according to claim 9, wherein a width of the guide portion gradually increases in the radial outward direction from the sample inlet hole.

16. The apparatus for analyzing sample according to claim 9, wherein:

the chamber includes a sample chamber communicating with the sample inlet hole; and the residual sample receptacle is separated from the sample chamber.

17. The apparatus for analyzing sample according to claim 9, wherein an upper end of the barrier is bent in a radial inward direction of the platform.

18. An apparatus for analyzing sample comprising:

a disk-shape platform comprising:

a chamber;

a sample inlet hole which is formed in an outer surface of the platform and through which a sample is injected to the chamber;

a residual sample receptacle which receives a residual of the sample present on the outer surface of the platform and is isolated from the chamber;

an opening which is formed in the outer surface of the platform at a position radially outward from the sample inlet hole and is arranged to receive the residual of the sample present on the outer surface of the platform and to introduce the received residual of the sample into the residual sample receptacle; and a protrusion which extends from the outer surface of the platform and surrounds the sample inlet hole.

19. The apparatus for analyzing sample according to claim 18, wherein the disk-shaped platform further comprises a slope portion which extends between the sample inlet hole and the opening, and is inclined downward in a radial outward direction.

20. The apparatus for analyzing sample according to claim 18, wherein the protrusion guides the residual of the sample into the opening.

* * * * *